United States Patent [19]
Verona et al.

[11] Patent Number: 5,776,185
[45] Date of Patent: Jul. 7, 1998

[54] CARDIOVASCULAR GRAFT

[75] Inventors: Alessandro Verona, Via Griziotti 4 IT-20145, Milan; Giuseppe Poletti, Torino, both of Italy

[73] Assignee: Alessandro Verona, Milan, Italy

[21] Appl. No.: 817,969

[22] PCT Filed: Sep. 26, 1995

[86] PCT No.: PCT/EP95/03800

§ 371 Date: Mar. 26, 1997

§ 102(e) Date: Mar. 26, 1997

[87] PCT Pub. No.: WO96/09800

PCT Pub. Date: Apr. 4, 1996

[30] Foreign Application Priority Data

Sep. 27, 1994 [IT] Italy .................. TO94A0748

[51] Int. Cl.⁶ .................. A61F 2/06; A61F 2/24; A61F 1/10
[52] U.S. Cl. .................. 623/1; 623/2; 623/3
[58] Field of Search .................. 623/1, 2, 3, 11, 623/12, 900; 600/36; 606/194, 195, 198

[56] References Cited

U.S. PATENT DOCUMENTS

| | | | |
|---|---|---|---|
| 4,600,405 | 7/1986 | Zibelin | 623/3 |
| 4,728,328 | 3/1988 | Hughes et al. | 623/1 |
| 4,994,078 | 2/1991 | Jarvik | 623/3 |
| 5,123,919 | 6/1992 | Sauter et al. | 623/1 |
| 5,178,634 | 1/1993 | Ramos-Martinez | 623/1 |
| 5,290,227 | 3/1994 | Pasque | 623/3 |
| 5,609,626 | 3/1997 | Quijano et al. | 623/1 |

FOREIGN PATENT DOCUMENTS 8201644  5/1982  WIPO .................. 623/1

*Primary Examiner*—Debra S. Brittingham
*Attorney, Agent, or Firm*—Sughrue, Mion, Zinn, Macpeak & Seas, PLLC

[57] ABSTRACT

A prosthetic conduit for the surgical treatment of cardiovascular pathologies, that can be attached in particular to each of the coronary ostia, left and right (D, S) and to the aortic valved conduit (H), respectively, comprising two hollow terminal elements (2, 3) implantable, by means of respective sewing rings (9, 10), on a coronary ostium (D, S) and on the aortic valved conduit (H), and at least one removable tubular element (4) for the connection between said terminal elements (2, 3), that can be rotated through 360° with respect to them.

20 Claims, 6 Drawing Sheets

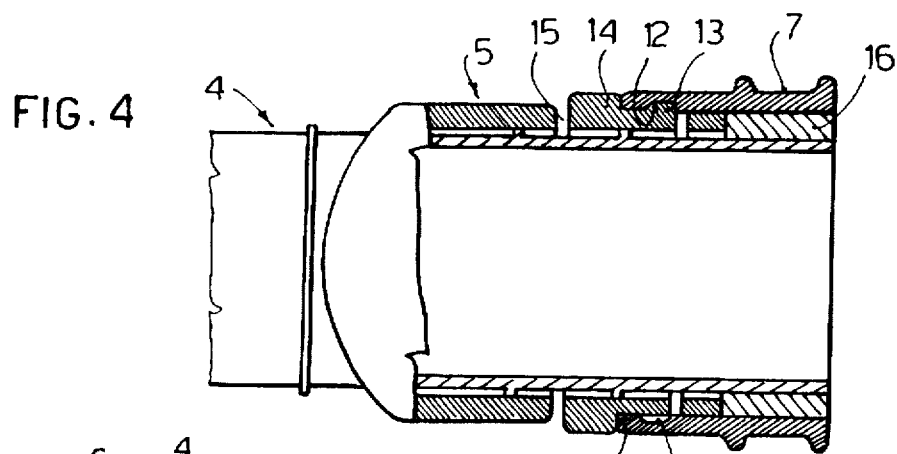
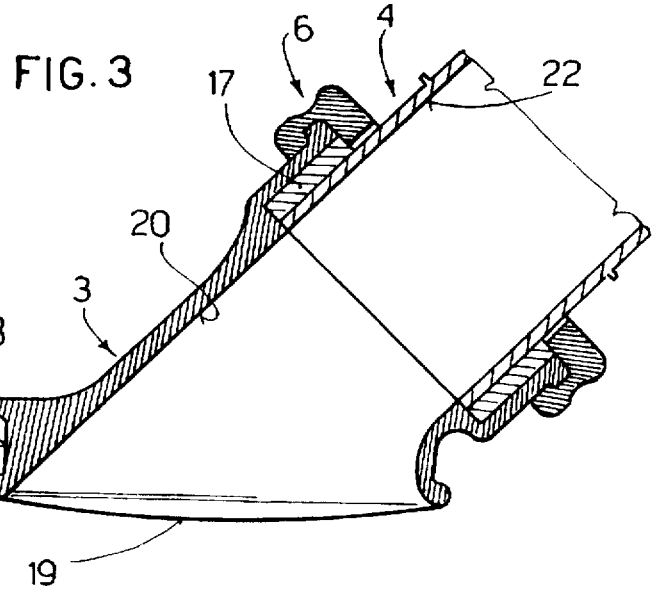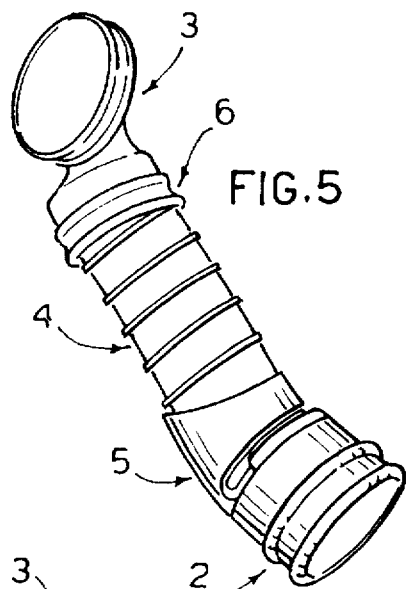
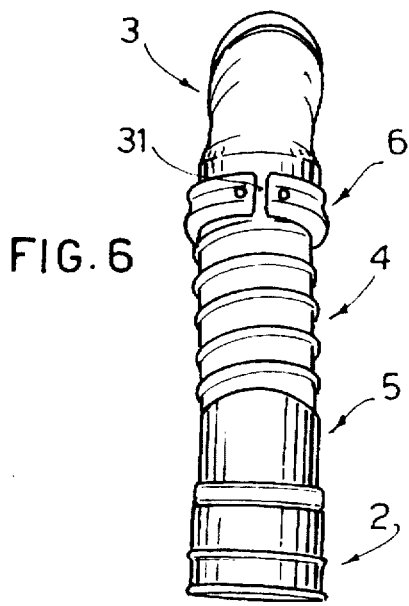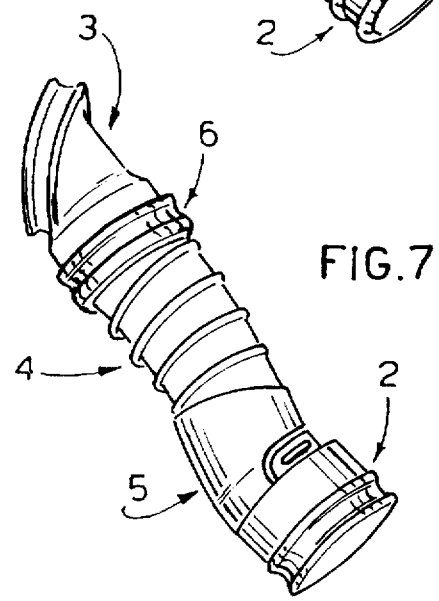

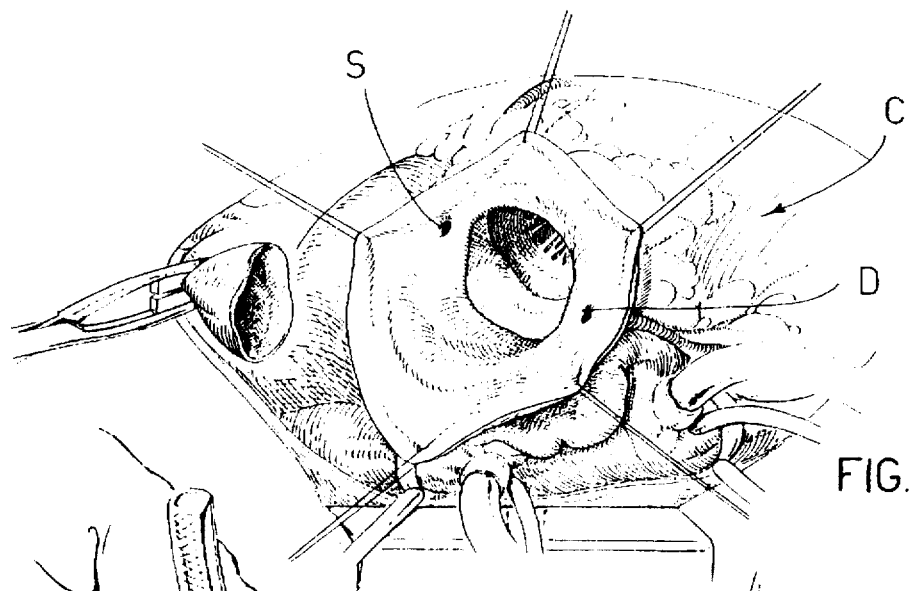
FIG. 8
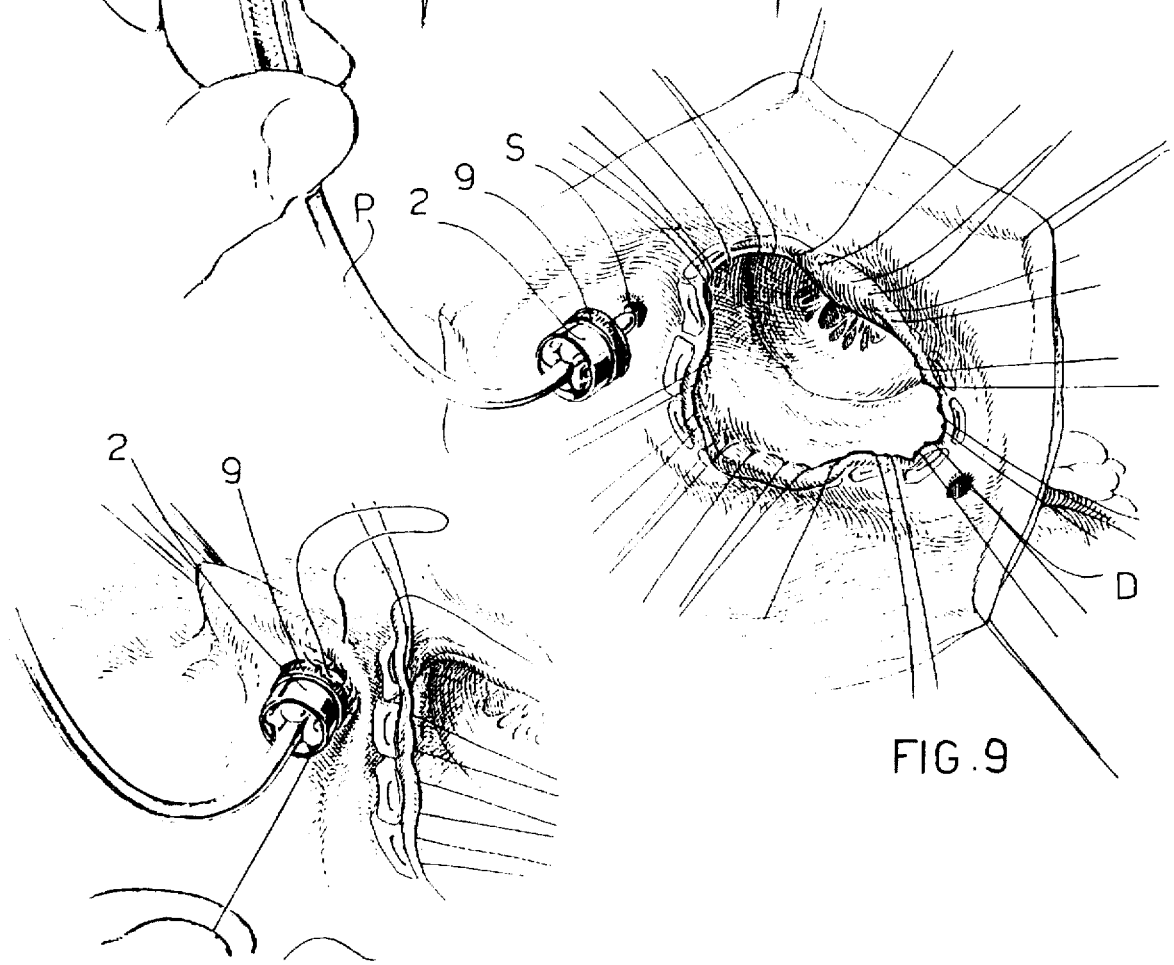
FIG. 9
FIG. 10

FIG. 11
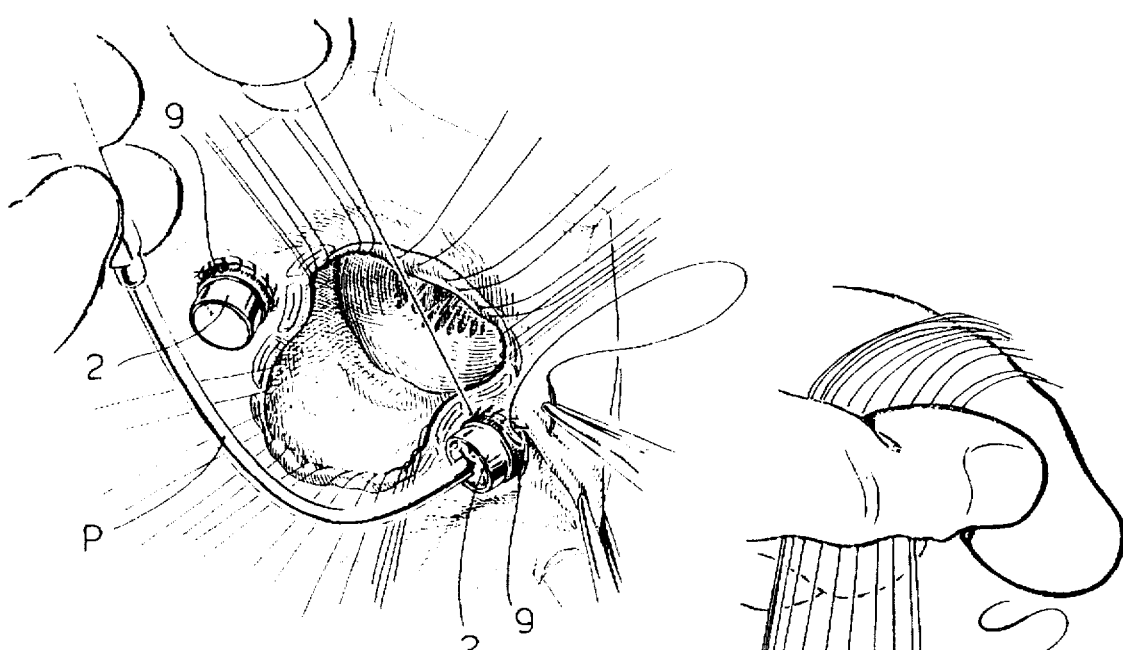
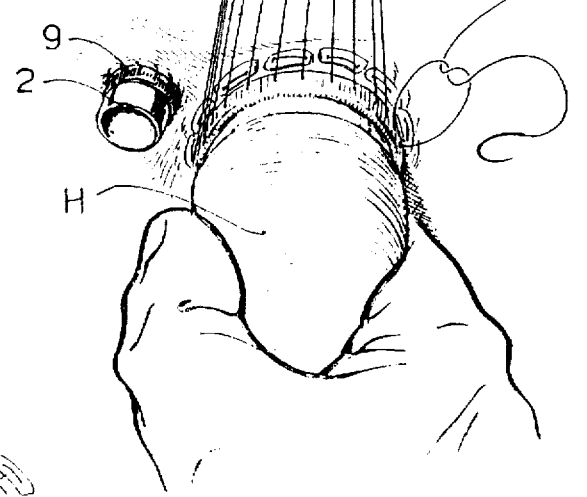
FIG. 12
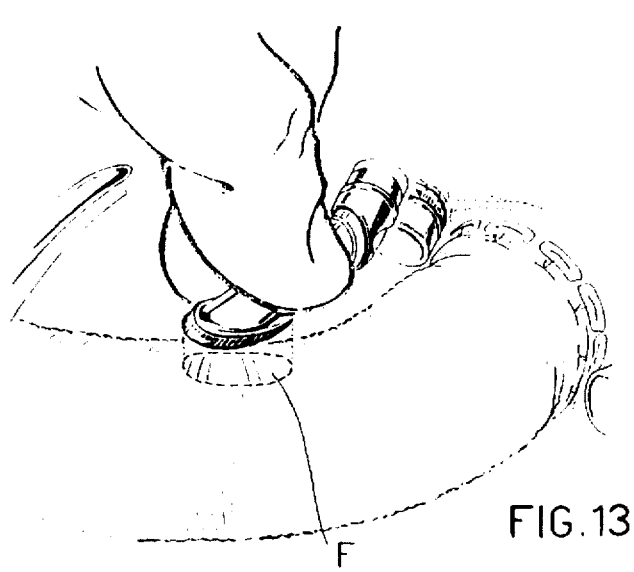
FIG. 13

CARDIOVASCULAR GRAFT

The present invention relates to prosthetic replacements designed for use in cardiovascular surgery or in vascular surgery in general.

Various serious pathologies dealt with by the cardiac surgeon involve dilatation or aneurysm of the ascending aorta associated with impaired function, or insufficiency, of the aortic valve.

The aim of surgical intervention is to replace the damaged anatomical structures, usually with prostheses.

A commonly used technique involves implantation of a prosthesis known as a composite graft or valved conduit consisting of a single structure that comprises a tubular portion, which replaces the ascending aorta, bearing at its proximal end an artificial cardiac valve, which replaces the aortic valve.

Composite grafts are commercially available in different sizes to allow them to be matched exactly to patients' anatomical structures.

A problem of fundamental importance for correct and complete execution of the surgical intervention arises from the concomitant re-establishment of coronary circulation to the heart, in that:

as is known, the coronary arteries are the blood vessels that ensure oxygenation of the heart and hence its vitality.

The coronary arteries originate from the most proximal segment of the ascending aorta, through two openings, the coronary ostia, one right and the other left, situated in an anatomically well defined position on the aortic wall. The coronary arteries originate from the ascending segment of the aorta; since said segment is affected by the pathological process of aneurysm, and therefore is also subject to replacement, the need arises to reattach the coronary artery origins to the tubular portion of the composite graft.

Whilst there is almost unanimous agreement amongst specialists in the field on the use of and implantation technique for the aortic composite graft, the ideal method for coronary reattachment has not yet been developed. The currently employed techniques have given rise to controversy as regards their intraoperative reliability and late results.

In brief, two main approaches can be identified:

A) Direct reattachment of the coronary ostia to the valved conduit;

B) Interposition of prosthetic material for the connection between the valved conduit and the coronary ostia.

The following techniques belong to group A):

A1) "Bentall-De Bono, Edwards-Kerr": consists in direct reattachment of the coronary artery origins on to the valved conduit, using the residual aortic wall which is brought over, the prosthetic conduit (so-called wrapping). The problems related to this technique are intraoperative bleeding, coronary artery dehiscence and false aneurysms.

A2) "Aortic button technique": consists in mobilisation of the coronary arteries from their site and re-implantation of the coronary ostia on the valved conduit as separate buttons. The disadvantages of this technique are the risk of injury of the coronary vessels or the pulmonary artery during the isolation procedure; the inaccessibility of the left coronary artery anastomosis which makes it difficult to control bleeding, should it occur.

The Cabrol technique belongs to group B) and consists in the use of a commercially available tubular vascular graft made of woven material known by the name of Dacron®; this graft is sutured, at its ends, to each coronary origin and connected to the valved conduit by suturing (side to side anastomosis). The result is a single orifice, instead of the original two, at the valved conduit that conveys the blood into the two branches of the graft destined for the respective coronary ostia.

The greatest problems with this technique are the possibility of kinking of the graft at the side to side anastomosis on the valved conduit and the possible formation of an angle with resulting occlusion of the right coronary branch of the graft.

Svensson's technique lies between group A) and group B) in that it uses the aortic button technique for the right coronary ostium and a modified Cabrol technique—only one graft branch—for the left coronary ostium.

WO 82/01644 describes a prosthetic conduit according to the preamble of appended claim 1. The parts of such conduit provide a fixed relation with respect to the conduit and therefore no orientation of the conduit is possible after assembling.

The aim of the invention is to overcome the drawbacks of the techniques described above and to create a prosthetic conduit especially for coronary reattachment that is extremely simple and reliable.

Another aim of the invention is to create a prosthetic conduit such that can be intraoperatively oriented even after the implant.

A further aim of the invention is to create a prosthetic conduit that can be easily replaced should the need arise.

These aims are achieved with the prosthetic conduit for the surgical treatment of cardiovascular pathologies according to the invention which has the characteristics listed in attached claim 1.

Preferred embodiments of the invention emerge from the dependent claims.

Substantially, the prosthetic conduit according to the invention comprises two hollow terminal elements that can be applied, for example by means of a sewing ring, to a coronary ostium and to the prosthetic aortic wall, and at least one removable tubular connecting element between said terminal elements.

The tubular element is advantageously flexible, and can rotate freely inside said terminal elements end to which it is connected by means of quick-lock coupling connections.

Further characteristics of the invention will be made clearer by the detailed description that follows, referring to a purely exemplary and therefore non limiting embodiment, illustrated in the attached drawings, in which:

FIG. 3 is a median section of the left terminal portion of the conduit in FIG. 2, taken along the plane of the figure itself;

FIG. 4 is a section taken along line IV—IV in FIG. 2;

FIGS. 5, 6 and 7 show the assembled prosthetic conduit in FIG. 2 in axonometric views from different angles;

FIG. 8 shows part of a heart which has undergone excision of the aortic valve and resection of the aneurysmal segment of the ascending aorta; the left and right coronary ostia are also visible;

FIG. 9 illustrates positioning of a terminal element of the prosthetic conduit according to the invention on the aortic wall surrounding the left coronary ostium;

FIG. 10 illustrates suturing of the terminal element illustrated in FIG. 9;

FIG. 11 illustrates positioning and suturing of another terminal element of the prosthetic conduit according to the invention at the aortic wall surrounding the right coronary ostium;

FIG. 12 illustrates suturing of an aortic valved conduit at the valve annulus;

FIG. 13 is a schematic view of the location of the opening to be made in the aortic valved conduit for connection of the prosthetic conduit according to the invention;

Figure 1:
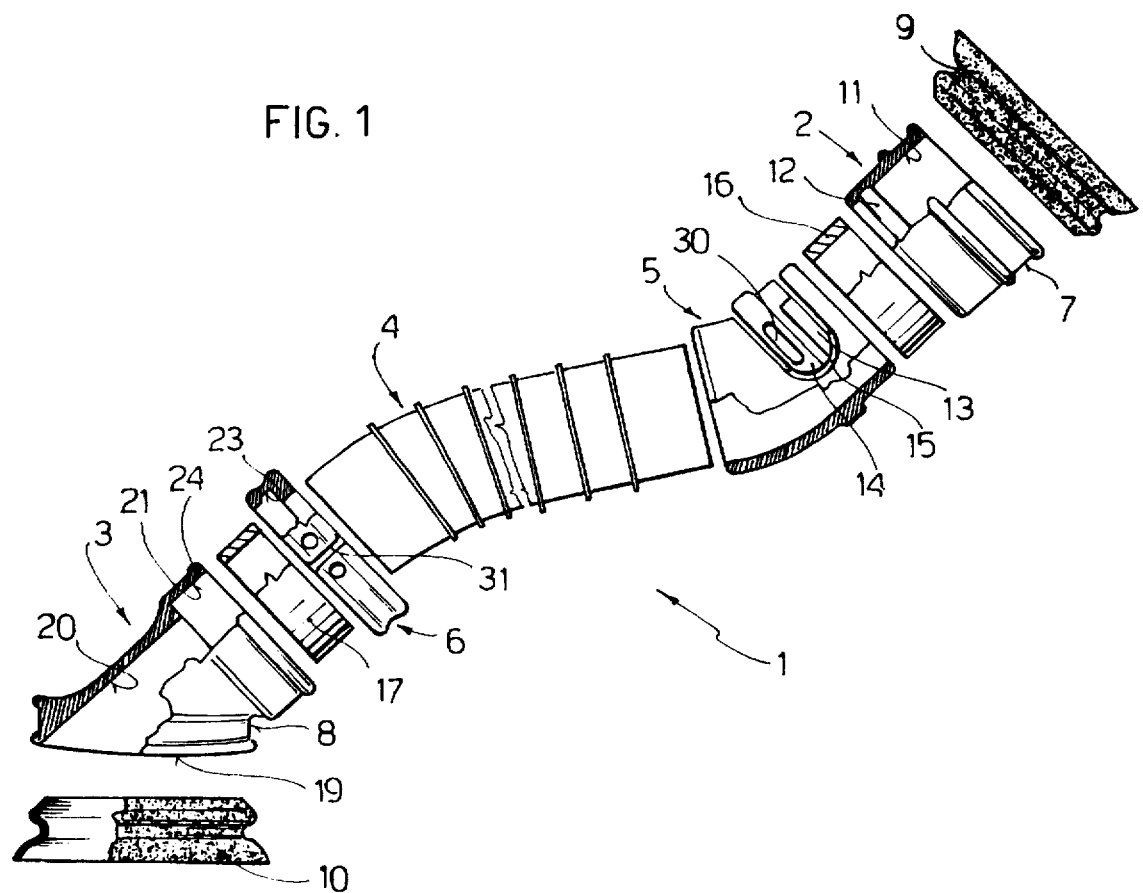
FIG. 1 is a partially sectional exploded view of a prosthetic conduit according to the invention.
Figure 2:
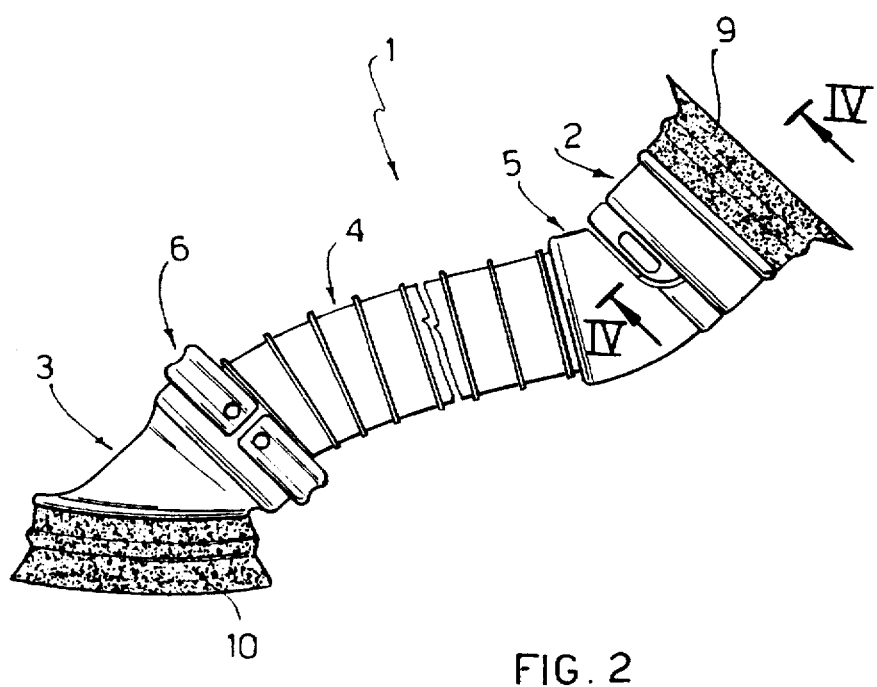
FIG. 2 is a view of the prosthetic conduit in FIG. 1 in the assembled state.

With reference now to FIGS. 1 to 7, the structure of the prosthetic conduit according to the invention will be described in its preferred embodiment.

The prosthetic conduit according to the invention has been indicated as a whole by the reference number 1. It comprises two hollow terminal elements, 2, 3 respectively, between which an intermediate tubular element 4 is connected, by means of respective elements 5, provided with quick-lock coupling systems, as will be better described below.

Each hollow terminal element 2, 3 has a corresponding annular groove 7, 8 to retain a respective suturable ring 9, 10, made of material such as Dacron® or Teflon®, and in any case such as to allow a suture needle to pass through it.

The hollow terminal element 2 is intended to be implanted on a coronary ostium by means of the sewing ring 9. It is substantially cylindrical in shape and has a inner surface 11 that is completely smooth except for an annular groove 12 provided in proximity to the end of it facing the tubular element 4 and able to engage with at least one raised part 13 provided on an elastic tab 14, created by making a substantially U-shaped cut 15 in the coupling element 5.

The element 5 has a curved elbow shape and is fitted on the tubular element 4, where it is retained by a rigid or semi-rigid end ring 16 provided on the tubular element 4, of which it is an integral part or to which it is applied. A similar ring 17 is provided at the other end of the tubular element 4.

After snap coupling, the hollow terminal element 2 is disposed against an edge 18 on the elbow-shaped element 5, so that the corresponding end of the tubular element 4 comes exactly level with the terminal element 2, as can be seen clearly from the section in FIG. 4, without causing any break in the continuity of the inner wall of the conduit.

The other hollow terminal element 3 of the prosthetic conduit 1 according to the invention is intended to be implanted, by means of the sewing ring 10, to the aortic graft and for this purpose it is cut slantwise 19, to adapt to the connection with the aortic valved conduit.

The hollow terminal element 3 has a smooth inner wall 20, with a sunken cylindrical seat 21 to house the corresponding end ring 17 of the tubular element 4, so that no break in continuity is caused between said inner wall 20 of the element 3 and the inner wall 22 of the tubular element 4, as can be seen from the section in FIG. 3.

The element 6 for attachment of the tubular element 4 to the terminal element 3 is an open elastic ring that is disposed on the tubular element 4, behind the ring 17 and has an inner annular groove 23 that clips around a corresponding annular ridge 24 provided on the element 3, as can be seen more clearly from the section in FIG. 3.

As an alternative to what has been illustrated, the elastic ring 6 can form an integral part of the tubular element 4 or of the end ring 17.

This type of coupling of the tubular element 4 on both hollow terminal elements 2, 3 allows a free 360° rotation of the tubular element 4 with respect to said terminal elements 2, 3, which is extremely useful for correct orientation of the prosthetic conduit according to the invention during implantation. Moreover, the elbow shaped element 5 also can be rotated with respect to the terminal element 2, so that it is appropriately orientated during implantation of the prosthetic conduit.

The tubular element 4 is advantageously of a flexible type and is made of material such as Dacron® or Teflon® (ePTFE, that is expanded polytetrafluoroethylene) which may be spiralled, with one layer in the attached figures, or otherwise.

The tubular element 4 can also be made of a biological material (autologous, homologous or heterologous).

The hollow terminal elements 2 and 3 on the other hand are advantageously rigid, with coupling means like the respective elements 5 and 6, and are preferably made of titanium. However, they can be made of any biocompatible material, for example PTFE.

Thanks to the possibility of rotating the tubular element 4 with respect to the terminal elements 2 and 3, it can be positioned according to intraoperative requirements, even after the terminal elements 2 and 3 have been sutured.

Another important characteristic of the prosthetic conduit according to the invention is that the snap coupling of the tubular element 4 to the terminal elements 2 and 3 is of the reversible type, so the tubular element 4, together with elements 5, 6 fitted onto it, can easily be removed and replaced in the event of re-operation.

For this removal it-is sufficient to exert pressure on a special mark 30 provided on the elastic tab 14 to cause disengagement of the raised part 13 from the groove 12 and thus allow the hollow terminal element 2 to be slipped off. Likewise, it is sufficient to apply pressure to widen the opening 31 of the flexible ring 6 to cause disengagement of its inner groove 23 from the annular ridge 24 of the terminal element 2, and thus allow the tubular element 4 to be slipped off the terminal element 3.

Figure 18:
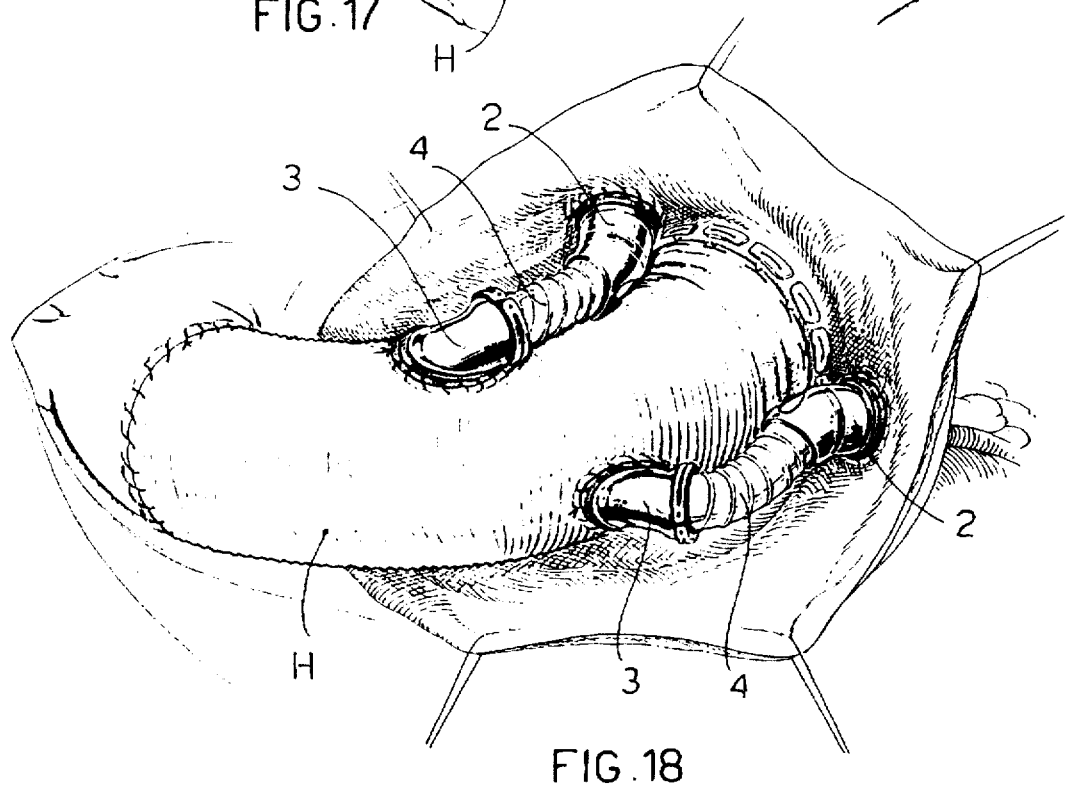
FIG. 18 illustrates two prosthetic conduits according to the invention, together with the aortic valved conduit, placed at the site of use.

FIGS. 8 and 18 illustrate schematically to and in sequence the basic stages of a surgical procedure for prosthetic replacement of the segment of ascending aorta and of the aortic valve.

In FIG. 8, C indicates part of a heart after excision of the aortic valve together with the aneurysmal section of the ascending aorta. In this figure the coronary ostia D and S, right and left, respectively, are also visible.

As can be seen in FIG. 9, a hollow terminal element 2 of the prosthetic conduit according to the invention is picked up using a positioning tool P and positioned at one of the coronary ostia, the left one S in the case illustrated, adjacent to the aortic wall surrounding the coronary ostium As illustrated in FIG. 10, the hollow terminal element 2 is sutured in place through the corresponding sewing ring 9.

FIG. 11 illustrates positioning, by means of the tool P, of another hollow terminal element 2 of a second prosthetic conduit, adjacent to the aortic wall surrounding the right coronary ostium D.

As can be seen in FIG. 12, a valved conduit H is inserted and sutured at the valve annulus in place of the aneurysmal section of aorta and the native aortic valve, which has been excised.

In FIG. 13 the aortic clamp is momentarily released in order to determine the site of a. hole F to be made in the tubular portion of the aortic valved conduit H , for connection of the prosthetic conduit 1 according to the invention.

Figure 14:
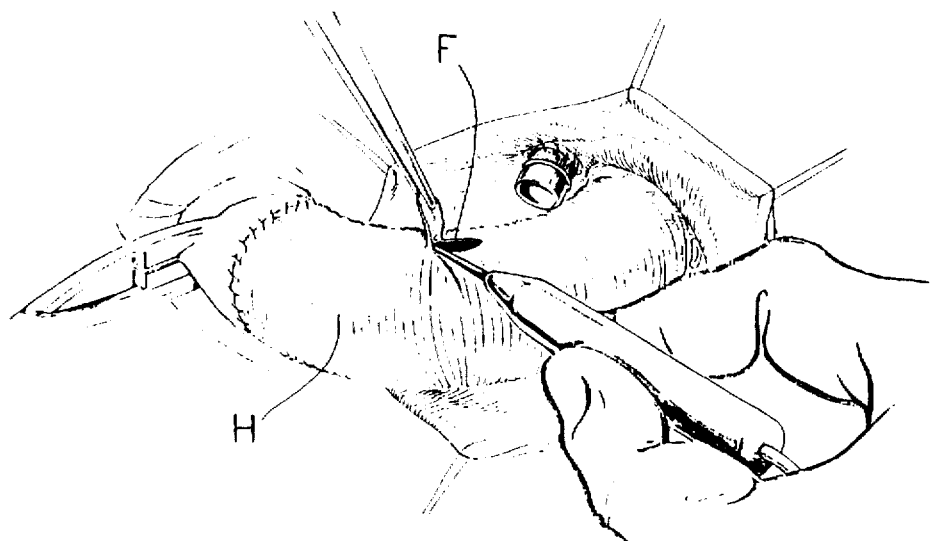
FIG. 14 illustrates execution of an opening on the aortic valved conduit.
Figure 15:
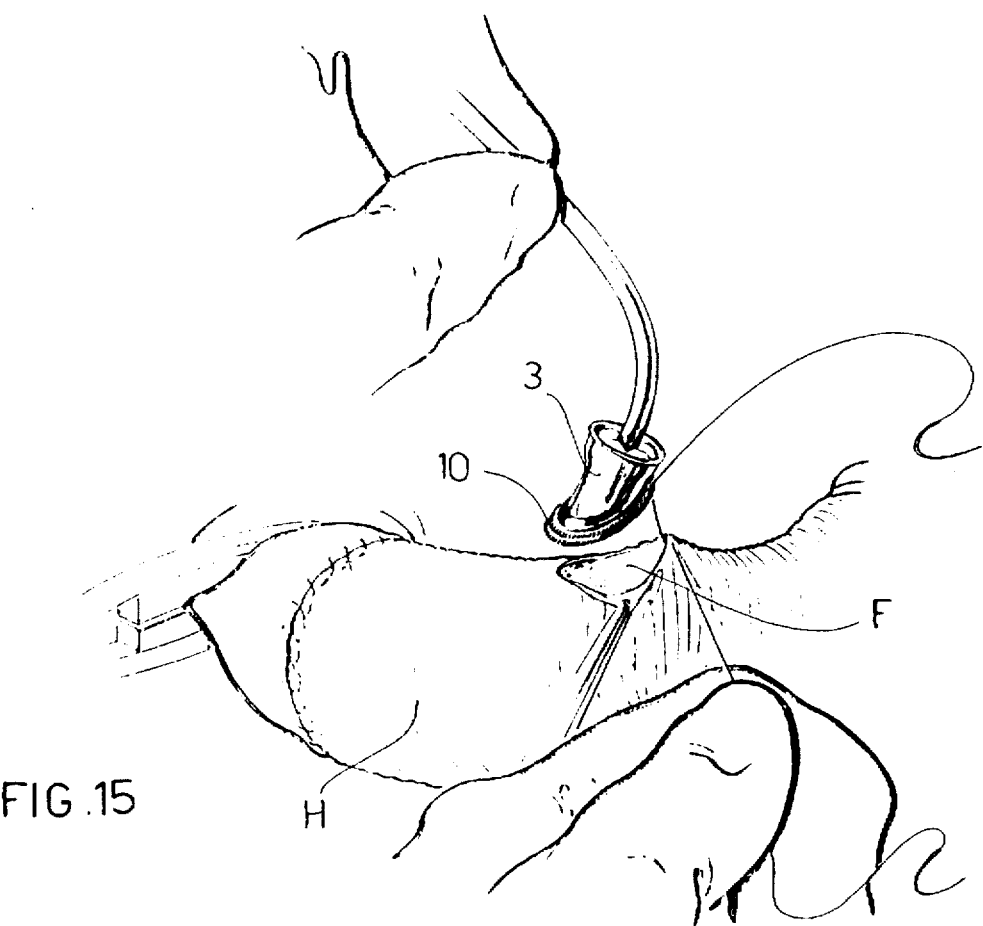
FIG. 15 illustrates a terminal element of the prosthetic conduit according to the invention during placement in the opening made in the valved aortic conduit.

In FIG. 14 the ascending aorta has been re-clamped distally and the hole F is made using a cautery knife or another suitable instrument.

A hollow terminal element 3 is then positioned and sutured, through the corresponding sewing ring 10, to the rim of the hole F.

Figure 16:
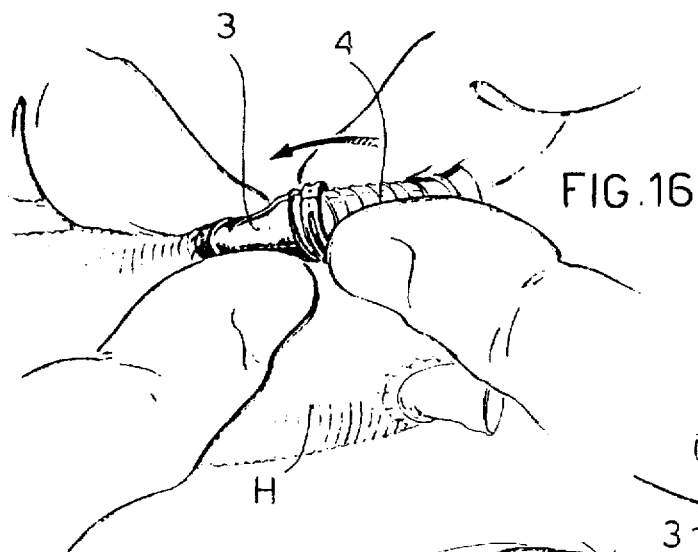
FIG. 16 illustrates fixation of a tubular element of the prosthetic conduit according to the invention to the terminal element of the aortic valved conduit.

FIG. 16 shows coupling of the tubular element 4 of the prosthetic conduit according to the invention to the terminal element 3.

Figure 17:
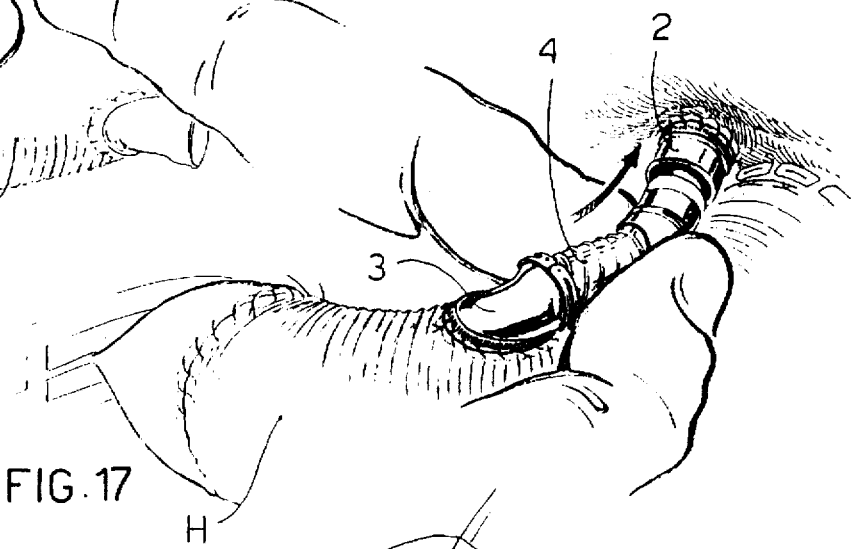
FIG. 17 illustrates fixation of said tubular element to the other terminal element attached to a coronary ostium.

FIG. 17 illustrates coupling of the tubular element 4 to the other terminal element 2, sutured at a coronary ostium Lastly, FIG. 18 illustrates two identical prosthetic conduits assembled in situ, one extending between the tubular part of the valved conduit H and the left coronary ostium S and one extending between the tubular part of the valved conduit H and the right coronary ostium D.

The sequence of phases described is obviously not binding for the purposes of the surgical procedure.

The composite structure of the prosthetic conduit I allows the best orientation thereof both with respect to the aortic conduit H and with respect to the coronary ostia D, S.

The slantwise cut surface 19 of the terminal element 3 perfectly matches the surface of the aortic conduit H, at a relative hole F.

The inner specular surface of the conduit 1 is devoid of breaks in continuity thanks to the structure of the reciprocal coupling systems connecting the various parts of the conduit. This remains true for any relative position imposed on the various parts, so that there is no hindrance to blood flow.

We claim:

1. An implantable prosthetic conduit for the surgical treatment of cardiovascular pathologies , that can be configured to be attached to each of the coronary ostia (D.S) and to the opening of an aortic valved conduit (H), comprising two hollow terminal elements (2, 3) that are adapted to be implanted on a coronary ostium (D.S) and on the valved aortic conduit (H), and at least one elongated tubular element (4) to connect said terminal elements (2, 3), that can be rotated about 360° with respect to said terminal elements after said terminal elements are fixed in place.

2. A prosthetic conduit according to claim 1, characterised in that said hollow terminal elements (2, 3) are substantially rigid.

3. A prosthetic conduit according to claim 1, characterised in that said tubular element (4) is flexible and capable of being elastically deformed.

4. A prosthetic conduit according to claim 1, further comprising sewable rings (9, 10) and being characterised in that said terminal elements (2, 3) are adapted to be implanted by suturing, through said sewable rings (9, 10).

5. A prosthetic conduit according to claim 1, characterised in that said tubular element (4) is defined by end portions and has at said end portions respective end elements (5, 6) for reversible quick-lock coupling to the corresponding terminal elements (2, 3).

6. A prosthetic conduit according to claim 5, characterised in that said coupling element (5) has a curved elbow shape and has an elastic tab (14) for engagement with and disengagement from the terminal element (2).

7. A prosthetic conduit according to claim 5, characterised in that said coupling element (6) is an open elastic ring.

8. A prosthetic conduit according to claim 5, characterised in that said coupling elements (5, 6) are fitted on said tubular element (4) and prevented from slipping off said tubular element by end rings (16, 17).

9. A prosthetic conduit according to claim 5, characterised in that said quick-lock couplings between the terminal elements (2, 3) and said tubular element (4) do not create breaks in the continuity in the inner surface of the conduit itself.

10. A prosthetic conduit according to claim 1, characterised in that said terminal element (3), implantable on the valved prosthetic conduit (H), has its end cut obliquely.

11. An implantable prosthetic conduit for the surgical treatment of cardiovascular and vascular pathologies, that can be configured to be attached to each of a first arterial blood vessel part and a second arterial blood vessel part respectively, comprising two hollow terminal elements (2, 3) that are adapted to be implanted on said first arterial blood vessel part and said second arterial blood vessel part, respectively, and at least one elongated tubular element (4) adapted to connect said terminal element (2,3), said element being rotatable about 360° with respect to said terminal elements after said terminal elements are fixed in place.

12. A prosthetic conduit according to claim 11, charasterised in that said hollow terminal elements (2, 3) are substantially rigid.

13. A prosthetic conduit according to claim 11, characterised in that said tubular elements (4) is flexible and capable of being elastically deformed.

14. A prosthetic conduit according to claim 11, characterised in that said terminal elements (2,3) are implanted by suturing, through respective sewable rings (9, 10), that form part of said terminal elements (2,3) or applied thereto.

15. A prosthetic conduit according to claim 11 characterised in that said terminal element (4) has at its respective ends elements (5, 6) for reversible quick-lock coupling to the corresponding terminal elements (2, 3).

16. A prosthetic conduit according to claim 11, characterised in that said coupling element (5) has a curved elbow shape and has an elastic tab (14) for engagement with and disengagement from the terminal element (2).

17. A prosthetic conduit according to claim 5, characterised in that said coupling element (6) is an open elastic ring.

18. A prosthetic conduit according to any one of the preceding claims, characterised in that said coupling elements (5, 6) are fitted on said tubular element (4) and prevented from slipping off it by respective end rings (16, 17), which are an integral part of said tubular element (4), or applied to it.

19. A prosthetic conduit according to claim 11, characterised in that said quick-lock couplings between the terminal elements (2, 3) and the intermediate tubular element (4) do not create breaks in the continuity in the inner surface of the conduit itself.

20. A prosthetic conduit according to claim 11, characterised in that said terminal element (3), implantable on the valved prosthetic conduit (H), has its end cut obliquely or slantwise.

* * * * *